United States Patent [19]
Clement

[11] Patent Number: 5,282,790
[45] Date of Patent: Feb. 1, 1994

[54] CANNULA SEALING MECHANISM

[75] Inventor: Thomas P. Clement, Bloomington, Ind.

[73] Assignee: Mectra Labs, Inc., Bloomfield, Ind.

[21] Appl. No.: 964,400

[22] Filed: Oct. 21, 1992

Related U.S. Application Data

[63] Continuation of Ser. No. 781,985, Oct. 24, 1991, Pat. No. 5,167,636.

[51] Int. Cl.⁵ .............................................. A61M 5/00
[52] U.S. Cl. ...................................... 604/167; 604/256
[58] Field of Search ................................ 604/167, 256

[56] References Cited

U.S. PATENT DOCUMENTS

| | | |
|---|---|---|
| 1,657,663 | 1/1928 | Devereux . |
| 4,000,739 | 1/1977 | Stevens . |
| 4,084,718 | 4/1978 | Wadsworth . |
| 4,096,860 | 6/1978 | McLaughlin . |
| 4,134,512 | 1/1979 | Nugent . |
| 4,149,535 | 4/1979 | Volder . |
| 4,240,411 | 12/1980 | Hosono . |
| 4,244,379 | 1/1981 | Smith . |
| 4,311,137 | 1/1982 | Gerard . |
| 4,334,551 | 6/1982 | Pfister . |
| 4,351,328 | 9/1982 | Bodai . |
| 4,422,860 | 12/1983 | Feinstein . |
| 4,424,833 | 1/1984 | Spector et al. . |
| 4,430,081 | 2/1984 | Timmermans . |
| 4,436,519 | 3/1984 | O'Neill . |
| 4,475,548 | 10/1984 | Muto . |
| 4,496,348 | 1/1985 | Genese et al. . |
| 4,540,411 | 9/1985 | Bodicky . |
| 4,585,440 | 4/1986 | Tchervenkov et al. . |
| 4,606,347 | 8/1986 | Fogarty et al. . |
| 4,610,665 | 9/1986 | Matsumoto et al. . |
| 4,626,245 | 12/1986 | Weinstein . |
| 4,649,904 | 3/1987 | Krauter et al. . |
| 4,655,752 | 4/1987 | Honkanen et al. . |
| 4,673,393 | 6/1987 | Suzuki et al. . |
| 4,705,511 | 11/1987 | Kocak . |
| 4,722,725 | 2/1988 | Sawyer et al. . |
| 4,758,225 | 7/1988 | Cox et al. . |
| 4,781,702 | 11/1988 | Herrli . |
| 4,798,594 | 1/1989 | Hillstead . |
| 4,809,679 | 3/1989 | Shimonaka et al. . |
| 4,813,938 | 3/1989 | Raulerson . |
| 4,817,631 | 4/1989 | Schnepp-Pesch et al. . |
| 4,842,591 | 6/1989 | Luther . |
| 4,857,062 | 8/1989 | Russell . |
| 4,874,377 | 10/1989 | Newgard et al. . |
| 4,874,378 | 10/1989 | Hillstead . |
| 4,886,507 | 12/1989 | Patton et al. . |
| 4,895,346 | 1/1990 | Steigerwald . |
| 4,895,565 | 1/1990 | Hillstead . |
| 4,909,798 | 3/1990 | Fleischhacker et al. . |
| 4,917,668 | 4/1990 | Haindl . |
| 4,929,235 | 5/1990 | Merry et al. . |
| 4,935,010 | 6/1990 | Cox et al. . |
| 4,950,257 | 8/1990 | Hibbs et al. . |
| 4,960,412 | 10/1990 | Fink . |
| 4,966,588 | 10/1990 | Rayman et al. . |
| 4,978,341 | 12/1990 | Niederhauser . |
| 5,000,745 | 3/1991 | Guest et al. . |
| 5,053,015 | 10/1991 | Gross . |
| 5,059,186 | 10/1991 | Yamamoto et al. . |
| 5,167,636 | 12/1992 | Clement ............................ 604/167 |

FOREIGN PATENT DOCUMENTS 3042229  5/1982  Fed. Rep. of Germany .

Primary Examiner—Paul J. Hirsch
Attorney, Agent, or Firm—Barnes & Thornburg

[57] ABSTRACT

A sealing assembly for sealing a cannula used in medical procedures is provided. The cannula is configured to allow passage therethrough of medical devices. The cannula is attached to a conduit piece formed to define at least one channel. A compressible annular seal is positioned in the at least one channel to allow passage through its central aperture of a medical device. A mechanism is provided for compressing the compressible annular seal to provide an airtight seal across the at least one channel. A duckbill flap valve is also positioned in the at least one channel adjacent to the compressible annular seal to receive the medical device after its insertion through the central aperture of the compressible annular seal.

12 Claims, 2 Drawing Sheets

CANNULA SEALING MECHANISM

This is a continuation of U.S. patent application Ser. No. 07/781,985 filed Oct. 24, 1991, now U.S. Pat. No. 5,167,636.

BACKGROUND AND SUMMARY OF THE INVENTION

This invention relates to a sealing assembly for sealing cannulas used in medical procedures. More particularly, the present invention relates to medical cannulas configured to allow passage of medical devices therethrough while maintaining an airtight seal.

Laparoscopic surgical procedures typically involve pneumatic inflation of a patient's abdominal cavity to increase the accessibility of organs in the abdominal cavity. A cannula is positioned to extend through the abdominal wall of the patient, and secondary cannulas, including graspers, tweezers, baskets, or other medical devices can be inserted through the cannula to manipulate abdominal organs. To prevent egress through the cannula of air or liquid from the abdominal cavity of the patient, a mechanism for sealing the cannula is required. Such a sealing mechanism must still allow passage through the cannula of medical devices for efficient operation.

Mechanisms for sealing cannulas, tubes, channels, or the like are known in the art. For example, Patton et al., U.S. Pat. No. 4,886,507, describes a Y-connector for use in angioplasty procedures. The Y-connector has disposed in its main passage a socket that receives a Tuohy-Borst O-ring, and a cap with a spigot projecting from it. The cap is threaded onto an outside surface of a socket so that it can be screwed down to bring the spigot into contact with the Touhy-Borst ring to compress it. When the spigot is engaged with the Touhy-Borst ring, flow of blood around external surfaces of the ring, between the O-ring and the socket, is blocked. Axially spaced from, and in alignment with, the Touhy-Borst O-ring, is a membrane having a circular opening to receive and seal a catheter.

Krauter et al., U.S. Pat. No. 4,649,904, discloses a disposable seal having a luer lock and fitting for use with a biopsy channel of an andoscope. A seal is unitarily molded of a soft elastomer to have a double seal arrangement. The seal in formed by an aperture end wall and a one-way opening slit through a plate or web behind an end wall.

Hosono, U.S. Pat. No. 4,240,411, discloses a device for sealing an endoscope channel. The sealing device includes a hollow cylindrical member connected at one end to a proximal end of a channel disposed in the sheath of an endoscope, and a tubular member of an elastic material disposed in a hollow cylindrical member. The tubular member is connected at one and sealingly to another end of a hollow cylindrical member. The other end of the tubular member is bent to form a sealing portion that prevents air introduced into a body cavity from flowing back through the channel.

McLaughlin, U.S. Pat. No. 4,096,860, relates to an encatheter adapted for biaxial flow for receipt of a syringe at one end with the main axial passage interconnecting a plastic teflon insertion conduit at the other end and adapted for placement in a blood vessel with a needle. A valve member 38 is received in a cavity 24 defined in a hub 10. The valve member 38 includes a circular or cylindrical wall portion 40 tapering down to a nipple-like element 42 having a slit 44 therethrough. Ordinarily, the slit 44 is in a closed condition to provide for an elastomeric valving in the form of a one-way valve, so that flow can only take place after the valve member 38 has been separated by a tubular member passing therethrough, or by positive pressure.

Muto, U.S. Pat. No. 4,475,548, relates to a fitting for endotracheal apparatus to receive an endoscopic tube. A fitting 25 includes a foam body 31 embraced within a sleeve 30. The foam body 31 is slit end to end, preferably diametrally and preferably not to the edge, by a slit 46. The foam body 31 can be compressed both radially and axially.

Merry et al., U.S. Pat. No. 4,929,235, describes a self-sealing percutaneous tube (e.g. a catheter tube) having a sealing mechanism to prevent blood or fluid leakage. The sealing mechanism includes a space sealing gasket adapted to surround the tube, with a distal sealing element being planar and having a slit. A proximal sealing element is also provided, the proximal sealing element is conical, and has an annular opening at its distal and small end. Optionally, the percutaneous tube includes a side arm flushing member or a female luer lock connection at its proximal end.

O'Neill, U.S. Pat. No. 4,436,519, discloses a hemostasis valve that includes a body having a central passage. A seal having a central aperture therein is mounted in the central passage, along with a diaphragm having a wall member with a slit therein. The diaphragm wall member has an inner bottom diaphragm surface, an outer diaphragm surface, and the slit extends from the inner bottom diaphragm surface to the outer bottom diaphragm surface. Catheters can be forced through the diaphragms' slit and can be withdrawn, allowing the diaphragm slit 12 to close.

Other types of hemostasis valves are known. For example, hemostasis valves are disclosed U.S. Pat. No. 5,000,745; U.S. Pat. No. 4,430,081; U.S. Pat. No. 4,626,245; and, U.S. Pat. No. 4,000,739.

Other valves for use in medical instruments, tubing, and/or stoppers or chromatographic injectors are disclosed in, for example, U.S. Pat. No. 4,673,393; U.S. Pat. No. 4,084,718; U.S. Pat. No. 4,515,752; U.S. Pat. No. 4,422,860; and, U.S. Pat. No. 4,013,310.

A sealing assembly for sealing a cannula used in medical procedures is provided. The cannula is configured to allow passage therethrough of medical devices. Contemplated medical devices can include secondary cannulas for injection or extraction of fluids, needles, graspers, tweezers, cutters, knives, baskets, or other conventional medical instrumentation. Typically, the cannula is disposable, and is attached to a disposable conduit piece formed to define at least one channel. Generally speaking, the present invention comprises a unique combination of compressible annular seal valve and a flap-type valve (such as a two-flap duckbill valve) in series with the annular seal valve to allow opening and closure of the one channel and sealably permit passage of medical instruments through said channel.

A compressible annular seal is positioned in the at least one channel to allow passage through its central aperture of a medical device. A mechanism is provided for compressing the compressible annular seal to provide an airtight seal across the at least one channel. Preferably, this mechanism is reversible, so that the seal can be allowed to return to its uncompressed state after withdrawal of the medical device.

In addition to the compressible annular seal, a secondary sealing mechanism that includes a flap valve (such as a two-flap duckbill valve) is provided. The duckbill flap valve is positioned in the at least one channel adjacent to the compressible annular seal to receive the medical device after its insertion through the central aperture of the compressible annular seal. The duckbill flap valve has at least first and a second flaps biased to sealingly engage each other, with the first and second flaps being configured to move apart to permit passage therethrough of a medical device inserted through the channel of the conduit piece.

In preferred embodiments, the compression mechanism of the sealing assembly includes a first annular wall defined by the conduit piece. A movable compression piece is formed to define a second annular wall, with the movable compression piece being movable with respect to the conduit piece to compress the compressible annular seal between its second annular wall and the first annular wall. Preferably, the movable compression piece is screwingly attached to the conduit piece by provision of external threads on the conduit piece, and internal threads on the movable compression piece to threadingly engage the external threads of the conduit piece.

Provision of an intermediary conduit piece optionally having multiple fluid passageways is not required for practice of the present invention. Alternatively, the present invention is a sealing assembly for pneumatically sealing a channel defined through a disposable cannula used in medical procedures, with the channel of the disposable cannula allowing passage therethrough of medical devices. The sealing assembly includes a compressible annular seal for sealing the channel, a mechanism for compressing the compressible annular seal to provide an airtight seal around a medical device inserted through the compressible annular seal, and a duckbill flap valve positioned adjacent to the compressible annular seal. The duckbill flap valve has first and a second flaps biased to sealingly engage each other, the first and second flaps being configured to move apart to permit passage therethrough of a medical device first inserted through the annular seal and into the channel of the disposable cannula.

DETAILED DESCRIPTION OF THE DRAWINGS

Figure 1:
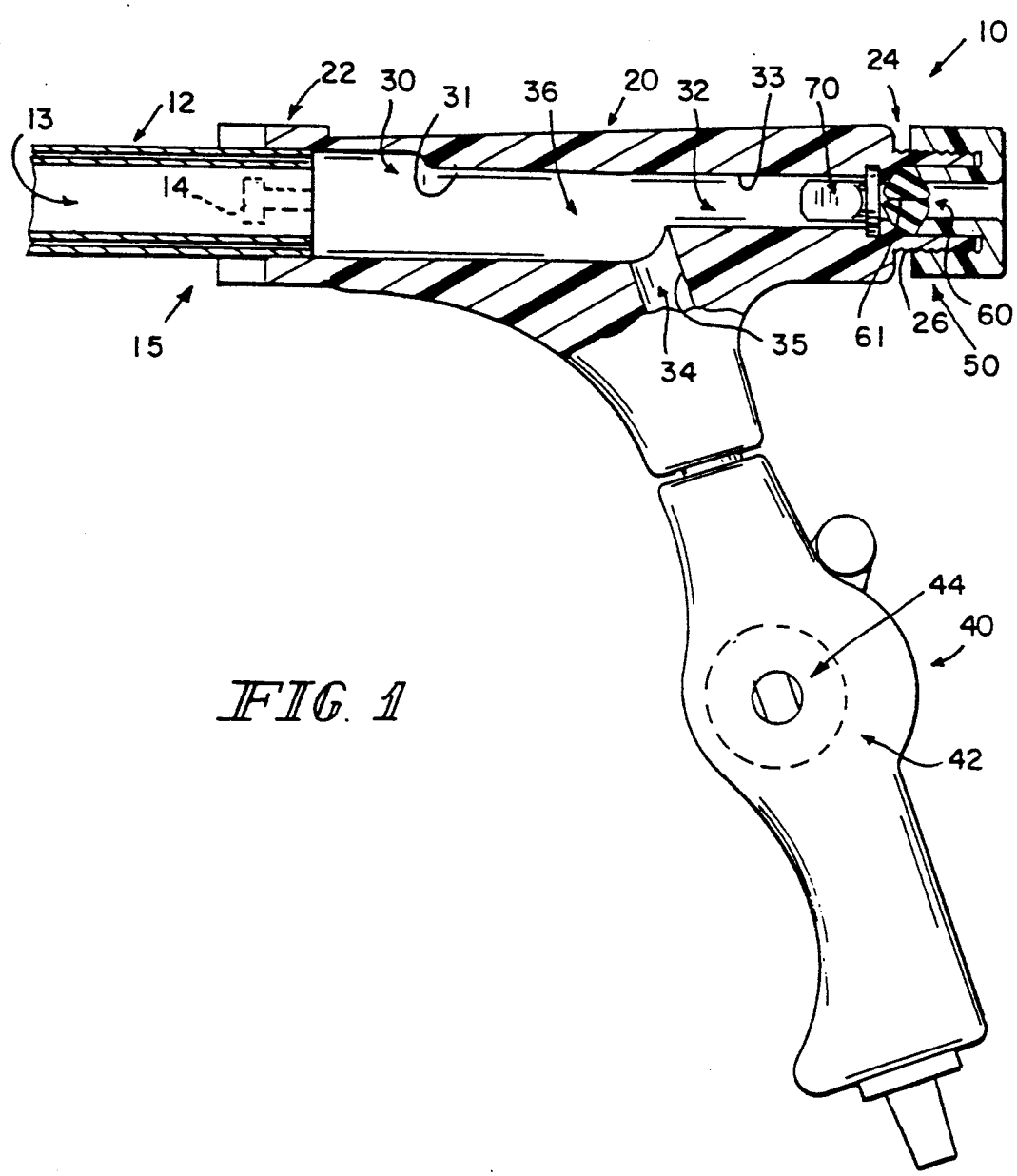
FIG. 1 is a side view of the cannula assembly, partially cut away to illustrate channels defined in an interior of a conduit piece, the channels of the conduit piece connecting to a cannula, to a valve mechanism, and to a sealing assembly that includes a compressible annular seal and a duckbill flap valve.

As illustrated in FIG. 1, a cannula assembly 10 includes a cannula 12 defining a channel 13. The cannula 12 is attached at and 15 to a conduit piece 20 by a lock element 14 configured to engage a matching lock element 22 defined by the conduit piece 20. Luer locks, friction coupling, tab engagement, snap fit attachment, threaded attachment, welded attachment (ultrasonic, RF, or thermal), adhesive attachment, or other conventional attachment methods known to those skilled in the art may be used to attach the cannula 12 to the conduit piece 20. Both removable or permanent attachment mechanisms are contemplated. Optionally, the cannula 12 can be integrally formed with the conduit piece 20.

The illustrated cannula 12 longitudinally extends for at least some portion of its length. Typically, the cannula 12 is substantially straight for it whole length, although curved, partially curved, or angled cannulas may be attached to the conduit piece 20. Typically, the cannula 12 has a tubular configuration, being formed to define a right cylinder having a circular cross section perpendicularly traverse to the longitudinally extending cannula length. However, the cross section can be elliptical, polygonal, or other art recognized cross sectional shapes.

For laparoscopic surgical procedures, a cannula 12 is typically dimensioned to have a length of about 200 centimeters to about 400 centimeters, and a cross sectional diameter of about 5 millimeters to about 20 millimeters. Preferably, the length of cannula 12 ranges from about 250 centimeters to about 300 centimeters, and its cross sectional diameter ranges from about 5 millimeters to about 10 millimeters. Dimensions may of course vary for use in non-laparoscopic surgery, being smaller or larger as required.

The cannula 12 is typically constructed from rigid materials such as surgical grade stainless steal or relatively rigid engineering-grade plastics such as polycarbonates. If the cannula is short, being less than about five centimeters, molded polyethylene or other common thermoplastics can be used to form the cannula, while still maintaining the required rigidity. Optionally, non-rigid, flexible cannulas can be connected to the conduit piece 20. Stiffener elements such an wires can be joined to such flexible cannulas to allow semi-permanent "bends" in the cannula.

The conduit piece 20 is formed to define a first passageway 30 having first passageway walls 31, a second passageway 32 having second passageway walls 33, and a third passageway 34 having third passageway walls 35. The channel 13 of the cannula 12 is directly attached in fluid connection to the first passageway 30. The first, second and third passagovays 30, 32, and 34 are dimensioned to permit passage of fluids (including air, vater, saline, body fluids) and solids (including body tissue and medical instruments). The passagavays 30, 32, and 34 are in cannon fluid cozounication, intersecting with each other at a branch 36.

Although metals such as stainless steel can be used to form the conduit piece 20, more commonly the conduit piece 20 is mold-formed as a single integral piece. Rigid thermoset plastics such as polycarbonate or polyethylene are preferred molding plastics. The low cost of molded plastics allows the conduit piece to be disposable, eliminating costly maintenance and sterilization procedures associated with manufacture of non-disposable conduit pieces. Optionally, construction of the conduit piece 20 from optically transparent plastics allows an operator to visually determine if one of the passageways 30, 32, or 34 is completely or partially blocked by solid tissue or other material.

The third passageway 34 of the conduit piece 20 is attached in fluid communication with a valving mechanism 40. The valve mechanism 40 includes a valve body 42 supporting a valve rotor 44 for ease of operation. Preferred valves are described in U.S. Pat. No. 5,019,054, to Clement et al., issued May 28, 1991, the disclosure of which is herein incorporated by reference.

Figure 2:
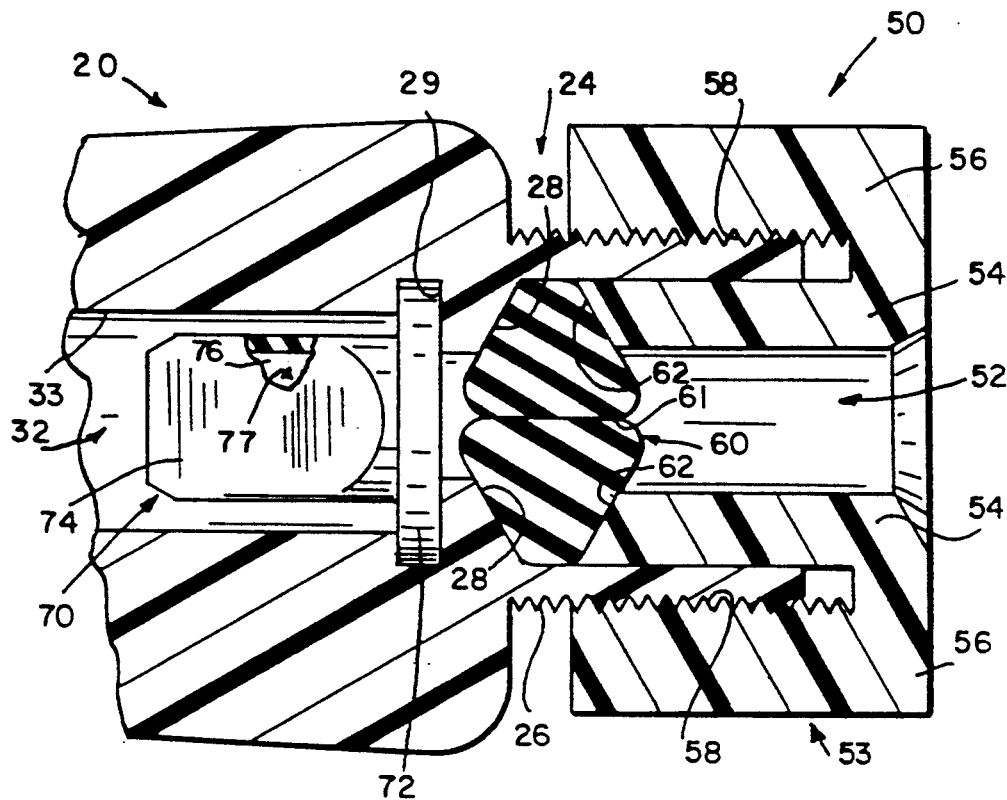
FIG. 2 is a magnified, side cross-sectional view of the sealing assembly illustrated in FIG. 1, showing complete closure of both the duckbill flap valve and the compressible annular seal.

A sealing assembly 50 is attached in fluid connection to the second passageway 32. An best seen in FIG. 2, which is an enlarged view of the sealing assembly 50 indicated in FIG. 1, the sealing assembly 50 includes a movable compression piece 53 having connected inner and outer annular portions 54 and 56, a compressible annular seal 60, and a duckbill flap valve 70. These elements cooperate to form an airtight seal when a medical device 80 (such as the secondary cannula shown in FIG. 3, or other conventional medical devices including graspers, tweezers, baskets, etc.) are inserted therethrough into the passageway 32 and cannula channel 13.

The compressible annular seal 60 is an annular 0-ring, normally having a central aperture 61 through which medical devices can be inserted. The seal 60 is constructed of natural or synthetic polymers (e.g. rubber, neoprene, etc.) that are elastically compressible. The seal 60 is illustrated in its fully compressed state in FIG. 2, with the movable compression piece 53 inwardly moved toward the conduit piece 20 to compress the seal 60 therebetween. Optionally, the seal 60 can be coated with friction reducing compounds, including inert, biocompatible silicone oils, fluorinated polymers, or other conventional friction reducers known in the art. Such friction reducing compounds can facilitate inward or outward longitudinal movement of the medical device 80 during its positioning in, or withdrawal from, the channel 13 of the cannula 12.

The compressible annular seal 60 is positioned in a channel 52 defined by an outwardly extending neck 24. The neck 24 is an integrally formed portion of the conduit piece 20, and is formed to present external threads 26 engagable by internal threads 58 defined an the outer annular portion 56 of the movable compression piece 53. The inner annular portion 54 fits into channel 52. Clockwise rotation of the movable compression piece 53 causes a screwing movement of the movable compression piece 53 toward the conduit piece 20, compressing the seal 60 between a first annular wall 28 defined in the conduit piece 20 and a second annular wall 62 defined in the inner annular portion 54 of the movable compression piece 53. Both wall 28 and wall 62 are directed to extend at an oppositely directed (mirror image), nonperpendicular angle relative to the longitudinally extending channels 52, 13, and longitudinally extending passageway 32, to maximize sealing compression.

Those skilled in the art will appreciate that other mechanisms for compressing the compressible annular seal 60 may be employed. For example, instead of screwing mechanisms, those skilled in the art may employ ratchet mechanism, levers, or clamps to move the movable compression piece 53 closer to the conduit piece 20. In addition, perpendicularly directed walls, curved, or multiple angled walls can be used to compress the seal 60.

Situated adjacent to the seal 60, and positioned in the passageway 32, is a duckbill flap valve 70. The duckbill flap valve 70 is integrally formed to have a first flap 74 biasingly directed in sealed engagement with a second flap 76. Both flaps 74 and 76 are integrally joined to a rim 72 having a central aperture 77 through which the medical device So can pass. The rim 72 is conformably fitted into an annular notch 29 defined in the second passageway walls 33 of the second passageway 32 to permanently hold the duckbill flap valve 70 in position. The flaps 74 and 76 are separated by a slit (not shown) that allows the flaps 74 and 76 to separate, moving apart an the medical device 80 is inserted therethrough. Like the seal 60, the flaps 74 and 76 can be coated with friction reducing compounds to ease insertion or withdrawal of the medical device 80. As those skilled in the art will appreciate, in addition to the described two-flap duckbill valve, multiple flap valves (including three or more biasingly engaged flaps) can be used in place of the duckbill valve. Alternatively, a single elastic flap positioned to biasing engage a conduit piece wall or projection is contemplated to be within the scope of the invention.

Figure 3:
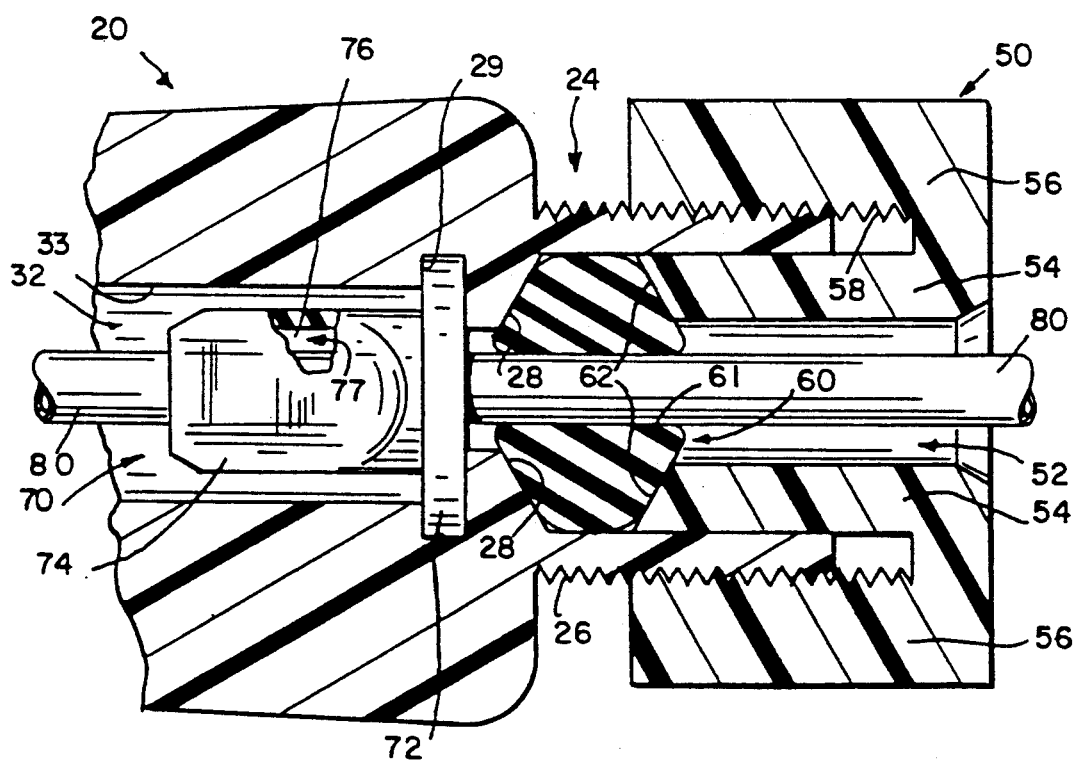
FIG. 3 is a side cross-sectional view of the sealing assembly, shown with a secondary cannula inserted through both the compressible annular seal and the duckbill flap valve to extend onward through the conduit piece and into the channel of the cannula illustrated in FIG. 1.

In operation, an illustrated in FIG. 3, the movable compression piece 53 is unscrewed counterclockwise until seal 60 is in a substantially uncompressed state. The tip (not shown) of the medical device So is inserted through the central aperture 61 of the seal 60. The compression piece 53 is then screwed clockwise to compress the seal 60, reducing the size of central aperture 61 and consequently providing an airtight seal against the medical device 80. The movable compression piece 53 is only moved inward far enough to provide an airtight seal by compressing the seal 60, and is not moved inward far enough to lockingly engage the medical device So. The medical device 80 is then pushed into the conduit piece 20, engaging and parting the flaps 74 and 76 of the duckbill valve. The medical device 80 can then be inserted through the second passageway 32, the first passageway 30, the channel 13 of the conduit 12, and to an operating site.

During withdrawal of the medical device 80, the tip (not shown) is brought back through the duckbill flap valve 70, allowing the flaps 74 and 76 to engage and seal against each other. Sealing engagement of the flaps 74 and 76 is encouraged by a positive pressure in the passageway 32 relative to atmospheric, but the biased construction of the flaps 74 and 76 promotes closure under neutral or even slightly negative pressures. The duckbill flap valve prevents outgassing of air or fluids (or an aerosol mixture of air and fluids) when the medical device So in pulled out through the central aperture 61 of the seal 60. After use, the cannula assembly 10 can be disposed of as medical waste.

As those skilled in the art will appreciate, it is not necessary to provide an intermediary channel piece, such as the conduit piece 20, to interconnect the cannula 12 and the sealing assembly 50. Alternatively, it is possible to directly connect the sealing assembly 50 to a conduit appropriately provided with external threads, or other conventional attachment mechanisms.

Although the invention has been described with reference to certain preferred embodiments, variations and modifications exist within the scope and spirit of the invention as described and defined in the following claims.

I claim:

1. A handheld-disposable device for use in laparoscopic surgery comprising:
   a conduit piece having first and second passageways in fluid communication with each other, the first passageway situated to allow the insertion of a medical device through the conduit piece and a second passageway communicating with the first passageway to allow a flow of fluid to be introduced into and withdrawn from the first passageway;

a valve controlling the flow of fluid through the second passageway into and out of the first passageway, the valve being operable by a digit of a surgeon's hand when holding the disposable device;

a cannula having a distal end and a proximal end, said proximal end being rigidly coupled to the first passageway of the conduit piece so that the medical device inserted through the first passageway of the conduit piece can be presented to the distal end of the cannula;

means for sealing the first passageway of the conduit piece, said sealing means permitting the medical device to be inserted through the first passageway of the conduit piece, the sealing means comprising a compressible annular seal;

a second valve positioned in the first passageway to provide a second sealing of the first passageway, said second valve being unaffected by compression of the annular seal; and wherein said conduit piece, valve, cannula, and sealing means are integrated into a rigid handheld disposable device.

2. The device of claim 1, wherein the second valve comprises a duckbill flap valve having first and second flaps configured to move apart to permit passage therethrough of the medical device.

3. The disposable device of claim 1, wherein the second valve is located downstream of and separated from the compressible seal and wherein the compressible seal can open to allow passage of the medical device and close around the medical device prior to the passage of the medical device into the second valve.

4. The disposable device of claim 2, wherein the flap valve is located downstream of and separated from the compressible seal and wherein the compressible seal can open to allow passage of the medical device and close around the medical device prior to the passage of the medical device into the second valve.

5. A handheld, disposable device for use in laparoscopic surgery comprising:

a conduit piece having a first passageway situated to allow the insertion of a medical device through the conduit piece and a second passageway communicating with the first passageway to allow fluids to be introduced into and withdrawn from the first passageway;

a valve controlling the flow of fluid through the second passageway into and out of the first passageway, the valve being operable by a digit of a surgeon's hand when holding the disposable device;

a cannula having a proximal end rigidly coupled to the first passageway of the conduit piece so that the medical device inserted through the conduit piece can be presented to a distal end of the cannula;

an annular compressible seal for forming an airtight seal around the medical device in the first passageway of the conduit piece when the medical device is inserted to permit fluid to flow between the distal end of the cannula and the second passageway; and a flap valve for sealing the medical device inserted in the first passageway which flap valve acts completely independently of forces on the compressible seal.

6. The device of claim 5, wherein the flap valve is positioned in the first passageway and configured to move apart to permit passage therethrough of the medical device.

7. The disposable device of claim 5, wherein the flap valve is located downstream of and separated from the compressible seal and wherein the compressible seal can open to allow passage of the medical device and close around the medical device prior to the passage of the medical device into the flap valve.

8. The disposable device of claim 6, wherein the flap valve is located downstream of and separated from the compressible seal and wherein the compressible seal can open to allow passage of the medical device and close around the medical device prior to the passage of the medical device into the flap valve.

9. A handheld, disposable device for laparascopic surgery comprising:

a cannular having a proximal end and a distal end for the passage of fluids and instruments into and out of the patient into which the cannula is inserted;

a conduit piece having a first passageway situated to allow the insertion of a medical device through the conduit piece and a second passageway communicating with the first passageway to allow fluids to be introduced into and withdrawn from the first passageway;

a valve controlling the flow of fluid through the second passageway into and out of the first passageway, the valve controlling the flow of fluid into and out of said cannula; and means for sealing said conduit piece passageways for admission and insertion of instruments through said conduit piece into said cannula to be presented at said cannula distal end, said means for sealing comprising a Touhy-Borst compressible seal to provide a seal around the medical instrument and a duckbill flap valve for sealing the medical device inserted in the first passageway which flap valve acts completely independently of forces on the compressible seal.

10. The device of claim 9, wherein the duckbill flap valve includes first and second flaps configured to move apart to permit passage therethrough of the instrument.

11. The disposable device of claim 9, wherein the duckbill flap valve is located downstream of and separated from the compressible seal and wherein the compressible seal can open to allow passage of the medical device and close around the medical device prior to the passage of the medical device into the duckbill flap valve.

12. The disposable device of claim 10, wherein the duckbill flap valve is located downstream of and separated from the compressible seal and wherein the compressible seal can open to allow passage of the medical device and close around the medical device prior to the passage of the medical device into the duckbill flap valve.

* * * * *